United States Patent [19]

Spadaro et al.

[11] Patent Number: 4,693,912
[45] Date of Patent: Sep. 15, 1987

[54] LYOPHILIZATION OF REAGENT-COATED PARTICLES

[75] Inventors: Anthony M. Spadaro, Mahopac; Thomas J. McLoughlin, Ossining; Phillip V. Engler, Tarrytown, all of N.Y.

[73] Assignee: Technicon Instruments Corporation, Tarrytown, N.Y.

[21] Appl. No.: 706,495

[22] Filed: Feb. 28, 1985

[51] Int. Cl.$^4$ .................. B01J 13/02; G01N 31/00; G01N 33/546

[52] U.S. Cl. .................. 427/213.3; 436/10; 436/17; 436/18; 436/533

[58] Field of Search ............. 427/213.3; 252/354; 436/8–19, 533

[56] References Cited

U.S. PATENT DOCUMENTS

| | | | |
|---|---|---|---|
| 3,780,195 | 12/1973 | Balassa | 427/213.3 |
| 4,102,808 | 7/1978 | Straka | 252/354 |
| 4,344,857 | 8/1982 | Shasha et al. | 427/213.3 |

*Primary Examiner*—Deborah L. Kyle
*Assistant Examiner*—T. J. Wallen
*Attorney, Agent, or Firm*—Morgan & Finnegan

[57] ABSTRACT

A method of lyophilizing reagent-coated latex particles which results in a product easily reconstituted without agglutination, retains activity, and remains stable and active at storage at 4° C.

32 Claims, No Drawings

LYOPHILIZATION OF REAGENT-COATED PARTICLES

BACKGROUND OF THE INVENTION

This invention relates to a novel lyophilization method for particles, e.g., latex particles, which may be reagent-coated, such that the lyophilized product reconstitutes to an unagglutinated suspension, and remains stable and active while stored at about 4° C. More particularly, this invention relates to a lyophilization procedure which employs the use of a cryoprotective agent which provides an inert amorphous network formed of macromolecular material which encapsulates the particles in spaced fashion and minimizes the "volume excluding effect" and, in addition, may include a zwitterionic buffer which neutralizes reactive but unprotected sites on the particles.

Often, reagents are coupled to reactive sites on the surface of particles, which may not be completely neutralized or blocked by the coupling reaction. It is evident that any residual reactive sites may eventually cause undesirable non-specific agglutination between the particles by bridging reactions.

In the past, the reconstitution of lyophilized reagent-coated particles, e.g., latex employed in particle-agglutinating immunoassays, had the severe disadvantage in that sonication of the reconstituted suspension was required to break up non-specifically agglutinated particles resulting from the effects of freeze-drying or lyophilization.

With the method of the present invention, it is possible to lyophilize particles, which may be reagent-coated, to preserve the activity of reagent and avoid spurious and non-specific agglutination of the particles to maintain the original state of agglutination of the suspension upon reconstitution. For example, if a monodisperse latex is lyophilized by the method of the invention, a substantially monodispersed latex suspension is obtained upon reconstitution.

SUMMARY OF THE INVENTION

In accordance with this invention, there is disclosed and claimed a method of lyophilizing reagent-coated particles which comprises:

(a) combining a suspension of reagent-coated particles with a cryoprotective agent, said cryoprotective agent forming, during lyophilization of said combined suspension, an inert network encapsulating said particles in spaced-apart, non-contacting relationship and also a zwitterionic buffer in an amount sufficient to substantially satisfy any reactive exposed sites on said particles; and (b) lyophilizing the combined suspension to provide a lyophilized product comprising said encapsulating network and which, upon reconstitution of said lyophilized product and dissolution of the encapsulating network, has a same degree of dispersity as the pre-lyophilized product.

The lyophilized products obtained by procedures herein discussed as well as the reconstituted products are within the scope of the present invention.

While the described preferred embodiment of the invention relates to reagent coated particles useful in immunoassays, it should be understood that the invention is applicable to the reversible lyophilization of particles, in general, which tend to self-agglutinate. For example, such method, can be used to lyophilize any latex particles, whether reactive or not, to produce reversible lyophilizates, i.e., solvent free powders of particles that revert to unagglutinated latex upon reconstitution with an appropriate solvent. The degree of dispersity of the reconstituted latex is substantially the same as that of the original pre-lyophilized suspension.

The practical significance of lyophilized products of the invention which can be described as freeze-dried latices, is that they can be stored at about room temperatures for prolonged periods and without bioprotectants. Such products can be formulated at will into reagents by diluting, with appropriate diluent(s) according to the desired applications. The method of the present invention provides for the long-term storage and preservation of said latices which may carry on their surface reactive groups (e.g., epoxy groups, chloromethyl groups, CNBr activated surface, etc.) that would degrade in the presence of solvent, e.g. by hydrolysis of active groups in the presence of water. Also, regarding radioactive immuno reagents, it would be advantageous in certain cases to supply the same in lyophilized form, to be reconstituted just prior to use.

The fact that dextran and other cryoprotectants useful in the practice of the invention are available in steryl and pyrogen free grades allows for the freeze-dried latices to be used for the formulation of reagents for injectable diagnostics in imaging and/or immunochemical identification of malignancies (e.g., by using fluorescent immunolatex or magnetic immunolatex prepared by lyophilization).

In one embodiment of this invention, a stabilizer is included in the suspension of the reagent-coated particles, typically, a serum albumin such as bovine serum albumin (BSA) or human serum albumin (HSA). The role of such stabilizer is to minimize adsorption of the particles to extraneous surfaces, e.g., the container wall, and to prevent denaturation of protein coated on the particles.

In another embodiment, the reagent-coated particles are derived, for example, from a polystyrene latex or a polyvinyl benzyl chloride latex.

The term "latex" as used in this specification designates a disperse system composed of at least two non-miscible materials at least one of them a liquid, characterized by the fact that the dispersed phase consists of substantially spherical particles (or droplets) of such small size (about 10 to 0.01 um) that their separation by sedimentation or creaming under the influence of ordinary (earth) gravitational forces requires prolonged periods of time (from hours to years). Because of the very high specific surface area associated with them (typically 1 to 100 $m^2$/gram of dispersed phase) latices are notorious for forming irreversible aggregates on drying requiring great forces for even partial redispersion. For this reason they are frequently used as adhesives and coherent coatings such as wall paint. If the variation of particle diameters is small (e.g. less than 10%) such latices are frequently referred to as "monodisperse".

Also, the reagent coated or conjugated to the particles may be an antibody or antigen to which there exists a corresponding antigen or antibody, the immunological reaction between said antibody and antigen being measurable, such as by particle counting, by change in light scattering or by visual observation of agglutination, for performing an immunoassay. Also, enzymes, dyes, toxins, fluorescent, phosphorescent and other luminescent materials may be coated on the particles to enhance the observation of any immunological reaction.

Representative antibodies include antibodies to thyroxin (anti-$T_4$), thyroid binding globulin, certain drugs such as phenolbarbital, phenytoin, theophylline, etc. Representative antigens include conjugates of such haptens as thyroxine, gentamycin, theophylline, digoxin, etc. and also antigenic proteins, e.g. thyroid binding globulin.

The preferred cryoprotective agent used in the practice of this invention is a straight chain polysaccharide having a molecular weight in the approximate range of 10,000 to 40,000. For instance, a dextran of molecular weight of about 10,000 may be used. Also, a branched polysaccharide, e.g., Ficoll Trademark of Pharmacia of molecular weight about 400,000, is suitable for use as the cryoprotective agent. Any bulking agent may be used as the cryoprotective agent in the practice of the present invention, which is inert and capable of forming an encapsulating network, as herein described, to maintain the particles separate during lyophilization.

When the particle suspension is a reactive latex, a zwitterionic buffer may be used to neutralize or treat exposed reactive sites on the particles. The zwitterionic buffer, preferably, contains amino groups, such as, cyclohexylaminoethanesulfonic acid (CHES), N-2-hydroxyethylpiperazine-N-2-ethanesulfonic acid (HEPES), N-tris(hydroxymethyl)methyl-2-aminoethanesulfonic acid (TES), N,N-bis(2-hydroxyethyl)-2-aminoethanesulfonic acid (BES) and 3-(N-morpholino)-propanesulfonic acid (MOPS). As is known, unreacted sites on latex particles can give rise to non-specific agglutination between the latex particles via a protein bridge. Neutralization of such reactive sites insures that the latex particles remain dispersed throughout the lyophilization process. Where no unprotected, reactive sites exist on the latex particles, a zwitterionic buffer need not be used.

In a further embodiment of this invention, there is disclosed and claimed a reversibly lyophilized latex product which, upon reconstitution, reverts to a suspension having the same degree of dispersity as the pre-lyophilized product. Preferably, no more than 20%, and more preferably, no more than 10% by weight of the reconstituted product contains agglutinated latex.

Detailed Description of the Invention

The preferred embodiment of the present invention provides a novel and unique method for lyophilizing reagent-coated particles, so as to retain both reagent activity and dispersity of the particle suspension. The process itself is characterized by insuring that the particles are maintained dispersed in suspension during the entire lyophilization process by incorporating in the particle suspension a cryoprotective agent. The cryoprotective agent has a molecular weight and concentration to minimize any "volume excluding effect" and establish a proper viscosity of the solvent to maintain the particles in suspension. The cryoprotective agent forms a protective, inert amorphous network which encapsulates the particles in spaced non-contacting fashion, thus preventing contact and non-specific agglutination of the particles. Also, a zwitterionic buffer in an amount sufficient to neutralize any exposed reactive sites on the latex particles is included. During the lyophilization process, the particle suspension is exposed to a rapid freezing cycle and a conservative lyophilization cycle, as hereafter described.

The "volume excluding effect" is the phenomenon that occurs when a water soluble polymer binds a fraction of water, which bonded fraction is not available for solvation of other solutes present in the medium. This effect should be minimized so as not to significantly alter the concentration of solutes in the medium. For this reason, the concentration of the cryoprotective agent should be low, but high enough to produce the network for encapsulating the particles during lyophilization. However, the concentration of the cryoprotective agent, at the same time, should be so high as to produce the network for encapsulating particles without introducing a significant volume excluding effect.

The incorporated zwitterionic buffer, in addition to satisfying the exposed reactive sites on the particles, acts in a buffering capacity to control pH changes which would adversely affect the activity of the antibody or antigen.

Prior to and during the lyophilization cycle, the reagent-coated particles are maintained in suspension within the liquid medium. Preferably, the specific gravity and/or size and concentration of the particles and/or the viscosity of the liquid medium are such that the particles tend to remain in suspension and not contact during lyophilization. During the initial cooling phase, when the liquid medium is subjected to a controlled freezing, the aqueous phase begins to crystallize and the concentration of the cryoprotective agent is increased to impart a much increased viscosity to the remaining liquid phase. The cryoprotective agent forms an amorphous network extending throughout the aqueous liquid medium, which ultimately encapsulates the latex particles in spaced or non-contacting relationship. The presence of the cryoprotective agent inhibits formation of large ice crystals during the freezing phase, thereby avoiding the particles being subjected to large forces which would tend to bring them into contact, whereby non-specific agglutination could result. By proper selection of the molecular weight and concentration of the cryoprotective agent, the volume excluding effect is minimized and proper viscosity of the liquid medium is established. Accordingly, the particles remain separated and do not tend to contact each other in the aqueous medium during lyophilization. As the ice mass continues to be formed, the presence of this amorphous network serves to maintain the particles separate. Fast freezing during the subsequent cooling phase tends to prevent large crystal growth in the solvent and, hence, to reduce pressures brought to bear on the particles during formation of the ice mass.

Upon sublimation of the ice mass, the amorphous network formed by the cryoprotective agent is essentially unaffected and continues to encapsulate the particles in spaced relationship. Preferably, sublimation is effected conservatively, i.e. at a very slow rate to avoid the formation of a liquid phase, so that desorption of water is gentle, and the possibility of protein damage is reduced. This avoids liquification of the ice mass, whereby the particles remain immobile in the amorphous network. The external dimensions of the lyophilized bulk are essentially the same as that of the initial ice mass. Even at room temperature, the lyophilized bulk remains as a "cake" and prevents the particles from contacting each other. Accordingly, the particles are prevented from contacting both prior to, during and subsequent to the lyophilization process, whereby the possibility of non-specific agglutination is very substantially reduced. In other words, the state of the reconstituted dispersion of the particles is the same as that of the original suspension before lyophilization, that is, the size distribution, including any agglutinated particles, would be substantially unaltered. Upon reconstitution, the lyophilized bulk, including the network formed by the cryoprotective agent, is dissolved and the particles again form a well-dispersed suspension. The dispersity of the reconstituted suspension is substantially the same as that of the original pre-lyophilized suspension. As is appreciated, the cryoprotective agent remains dissolved in the reconstituting medium and, therefore, should be inert with respect to any assay or reaction wherein the reagent-coated particles are to be used.

Also, non-specific agglutination of reagent-coated latex particles can result due to the presence of exposed unreacted sites on the surfaces thereof. A zwitterionic buffer agent is introduced into the aqueous medium, which has the capacity to neutralize exposed unreacted sites on the latex particles whereat a bond could be formed. Generally, such neutralization of reactive sites is effected prior to the lyophilization process and complements the effect of the cryoprotective agent during the lyophilization process to avoid non-specific agglutination between such particles.

EXAMPLE I

Preparation of $T_4$ Antibody Coated Latex for Lyophilization

1. Antibody coated latex is formulated in the following Buffer System a. 3-Cyclohexylaminoethane Sulfonic Acid (CHES), 0.5M
   b. Dextran T10 (molecular weight about 10,000) 1% by weight
   c. Bovine Serum Albumin 0.1% by weight
   d. Ficoll 400,000 M.W. 0.86 mg/ml
   e. 8-Anilino-1-Naphthalenesulfonic Acid, Ammonium Salt (ANS), 0.1 mg/ml (releasing agent)
   f. Tween 20 0.100% (surfactant)

The ingredients are weighed into a beaker of sterile distilled water filled with ½ the volume to be prepared and mixed gently on a magnetic stir plate.

2. pH Adjustment

The pH is adjusted to 9.75±0.1 with NaOH, Q.S. to the correct volumes.

3. Addition of $T_4$ Antibody Coated Latex (Vinyl Benzyl Latex)

a. The concentration of $T_4$ Antibody coated latex is obtained from a titration procedure that matches latex concentration to desired assay performance.
   b. The total volume of latex to be diluted is then determined by the batch volume to be prepared.
   c. The latex is centrifuged at a rate of 15,000 RPM on a Sorval RC2B with a S33 head, for 15 minutes. The supernatant is decanted and the remaining pelleted latex is resuspended to the titrated volume with the Buffer prepared above.
   d. Sonication is used to ensure a homogeneous suspension. Sonicate until pellet is completely broken up. Sonicate until the optical density of the latex remains constant.
   e. The latex is tested for $T_4$ inhibition performance and its state of agglutination, vialed then lyophilized according to the predetermined lyophilization cycle.

4. Lyophilization Cycle

The lyophilization cycle involves a first step of liquid-nitrogen freezing wherein the sample is cooled at a rate of 5° C./minute to −4° C., then cooled to −55° C. at a rate of 2° C./minute until all cyrstallized growth terminates, and finally cooled at a rate of 3° C./minute to −66° C.

The lyophilization cycle is completed by sublimation at a shelf temperature of −10° C. for 24–28 hours; and then at a reduced shelf temperature of +10° C. for about 40 hours.

5. Post Lyophilization

The product is acceptable since, upon reconstitution, it performs as the prelyophilization sample while remaining in a homogeneous unagglutinated suspension.

6. Reagent Acceptability

Acceptability of reagent-coated particles as disclosed herein, for example, the $T_4$ antibody coated latex is determined by the measure of particle dispersity (A) and reagent performance (B).

(A) The dispersity of the reagent is detected by the measurement of light scattering prior to and after lyophilization. Typically, this involves a measurement of absorbance of the suspension. It is found that using this method the absorbance of both pre- and post-lyophilizated reagent is substantially the same indicating that no substantial changes to dispersity, i.e. agglutination, occurred during the lyophilization process.

(B) The performance of reagent coated particles as disclosed herein, for example, $T_4$ antibody coated latex is measured by the amount of agglutination that occurs when the antibody coated latex reacts with its corresponding conjugated antigen. The degree of agglutination is detected by the light scattering properties as measured by absorbance. It was found that using this method the degree of specific immuno agglutination of both pre-and post-lyophilizated reagent is substantially the same indicating that no substantial changes to the product performance, i.e., the specific immuno agglutination of corresponding conjugated antigen to antibody coated latex, occurred during the lyophilization process.

EXAMPLE II

The procedure of Example I is repeated except that for component 1.b of the antibody coated latex is substituted the following materials:

| | | |
|---|---|---|
| (1) | Dextran T10 | 1% by weight and |
| | PVP (about 15,000 m. wt.) | 2.5% by weight |
| (2) | Dextran T10 | 1% by weight and |
| | PVP (about 30,000 m. wt.) | 2.5% by weight |
| (3) | Dextran T40 | 1% by weight and |
| | PVP (about 15,000 m. wt.) | 2.5% by weight |
| (4) | Dextran T40 | 1% by weight and |
| | PVP (about 30,000 m. wt.) | 2.5% by weight |

EXAMPLE III

The procedure of Example I is repeated except that in step 3 a polystyrene antibody coated latex is used in lieu of vinyl benzyl latex with similar results.

EXAMPLE IV

The lyophilized product obtained in Example I is used to assay for $T_4$ in a sample by measurement of light scattering changes associated with the inhibition of the antibody coated latex and its corresponding antigen conjugates as described in pending U.S. application Ser. No. 544,749 filed Oct. 24, 1983, commonly assigned.

Sample assay can also be measured by a particle agglutination counting immunoassay as described in Masson, P., et al, 1981, Methods Enzymol. 74, 106.

EXAMPLE V

The polyvinyl benzyl chloride latex particles used to prepare the reagent coated latex particles of Example I are subjected to the lyophilization cycle and post-lyophilization cycle described in Example I.

A comparison between the pre- and post-lyophilized products using the particle dispersity test (A) of Example I shows that the absorbance of the pre- and post-lyophilized products is substantially the same, indicating that no substantial changes in dispersity, i.e., agglutination, occurred during the lyophilization process.

It should be understood by those skilled in the art that various modifications may be made in the present invention without departing from the spirit and scope thereof as described in the specification and defined in the appended claims.

What is claimed is:

1. A method of lyophilizing reagent-coated particles, which comprises:
   (a) combining a suspension of reagent-coated particles with a cryoprotective agent, said cryoprotective agent forming, during lyophilization of said combined suspension, an inert network encapsulating said particles in spaced-apart non-contacting relationship and also a zwitterionic buffer in an amount sufficient to substantially satisfy any reactive exposed sites on said particles; and
   (b) lyophilizing the combined suspension to provide a lyophilized product comprising said encapsulating network and which, upon reconstitution of said lyophilized product and dissolution of the encapsulating network, has a same degree of dispersity as the pre-lyophilized product.

2. The method of claim 1, including the further step of reconstituting the lyophilized product by the addition of solvent.

3. The method of claim 1 wherein said particles are latex particles.

4. The method of claim 3 wherein said particles comprise a polystyrene latex.

5. The method of claim 3 wherein said particles comprise a polyvinyl benzyl chloride latex.

6. The method of claim 1, including the further step of introducing a stabilizer in said combined suspension.

7. The method of claim 6 wherein said stabilizer is a serum albumin.

8. The method of claim 7 wherein said serum albumin is bovine serum albumin (BSA) or human serum albumin (HSA).

9. The method of claim 1 wherein said reagent is an antibody.

10. The method of claim 9 wherein said antibody is anti-thyroxin (anti-$T_4$).

11. The method of claim 9 wherein said antibody is selected from the antibodies to theophylline, thyroid binding globulin, phenobarbital or phenytoin.

12. The method of claim 1 wherein said reagent is an antigen.

13. The method of claim 1 wherein said cryoprotective agent is a polysaccharide.

14. The method of claim 13 wherein said polysaccharide is a straight chain polysaccharide having a molecular weight in the approximate range of 10,000 to 40,000.

15. The method of claim 14 wherein said polysaccharide has a molecular weight of about 10,000.

16. The method of claim 15 wherein said polysaccharide is dextran.

17. The method of claim 13 wherein said polysaccharide is a globular polysaccharide.

18. The method of claim 17 wherein said polysaccharide is ficoll of molecular weight about 400,000.

19. The method of claim 1 wherein said cryoprotective agent is a mixture of polysaccharide and polyvinylpyrrolidone (PVP).

20. The method of claim 1 wherein said zwitterionic buffer is an amino acid buffer.

21. The method of claim 20 wherein said buffer is cyclohexylaminoethanesulfonic acid (CHES).

22. The method of claim 20 wherein said buffer is selected from N-2-hydroxyethylpiperazine-N-2-ethanesulfonic acid (HEPES), N-tris(hydroxymethyl)methyl-2-aminoethanesulfonic acid (TES), N,N-bis(2-hydroxyethyl)-2-aminoethanesulfonic acid (BES) or 3-(N-morpholino)propanesulfonic acid (MOPS).

23. The method of claim 1 wherein said reagent-coated particles comprise anti-$T_4$-coated polyvinyl benzyl chloride, said cryoprotective agent is dextran and said buffer is CHES which maintains a mixture pH in the range of about 7.0 to about 10.0.

24. The method of claim 23 wherein said lyophilization step comprises the three step freezing cycle of cooling at a rate of 5° C./minute to −4° C., cooling to −55° C. at a rate of 2° C./min. until crystallized growth terminates, and cooling at a rate of 3° C./min. to −66° C.

25. The method of claim 24 including a conservative drying cycle wherein no liquid phase is formed.

26. The method of claim 25 wherein said drying cycle comprises sublimation at a temperature of −10° C. for about 24–28 hours followed by treatment at about 10° C. for to about 40 hours.

27. The method of claim 1, including the further step of initially forming a substantially monodispersed suspension of said particles.

28. A method of lyophilizing particles which tend to agglutinate upon contact which comprises:
   (a) combining a suspension of said particles with a cryoprotective agent, said cryoprotective agent forming, during lyophilization of said combined suspension, a protective inert network encapsulating and maintaining said particles in spaced-apart non-contacting relationship, and
   (b) lyophilizing said combined suspension
   wherein the resulting lyophilized product exhibits, upon reconstitution, a same degree of dispersity as said combined suspension.

29. The method of claim 28 wherein the lyophilized product is reconstituted by the addition of a solvent.

30. A diagnostic kit for performing an assay determination which includes a product as claimed in claims 1, 2, 28 or 29.

31. The method of claim 28 wherein said cryoprotective agent has a molecular weight sufficiently low to minimize the volume excluding effect.

32. The method of claim 28 wherein said particles have unsatisfied reactive sites and including the further step of incorporating in said combined suspension an agent to satisfy said sites.

* * * * *